(12) United States Patent
Metzner et al.

(10) Patent No.: US 6,874,657 B2
(45) Date of Patent: Apr. 5, 2005

(54) BIOLOGICAL SEALANT STORAGE AND DISPENSING SYSTEM

(75) Inventors: Hubert J. Metzner, Marburg (DE); Stewart Madison Fox, Cambridge (GB)

(73) Assignee: ZLB Behring GmbH, Marburg (DE)

( * ) Notice: Subject to any disclaimer, the term of this patent is extended or adjusted under 35 U.S.C. 154(b) by 330 days.

(21) Appl. No.: 10/109,631

(22) Filed: Apr. 1, 2002

(65) Prior Publication Data

US 2002/0161335 A1 Oct. 31, 2002

(30) Foreign Application Priority Data

Apr. 2, 2001 (GB) .......................................... 0108207.2

(51) Int. Cl.[7] .............................. B67D 5/00; B67D 5/60
(52) U.S. Cl. ........................... 222/82; 222/88; 222/132; 222/135; 222/137; 222/145.1; 222/145.5; 222/327; 222/386; 222/391
(58) Field of Search ............................ 222/82, 88, 132, 222/135, 137, 145.1, 145.5, 326, 327, 386, 391; 433/90

(56) References Cited

U.S. PATENT DOCUMENTS

| | | | |
|---|---|---|---|
| 3,517,668 A | 6/1970 | Brickson | .................... 128/218 |
| 3,767,085 A | * 10/1973 | Cannon et al. | ................ 222/82 |
| 5,314,412 A | * 5/1994 | Rex | ............................ 604/191 |
| 5,370,273 A | * 12/1994 | Rohloff et al. | ............... 222/132 |
| 5,415,631 A | 5/1995 | Churinetz et al. | ............ 604/57 |
| 6,042,262 A | 3/2000 | Hajianpour | ................. 366/139 |

FOREIGN PATENT DOCUMENTS

| | | |
|---|---|---|
| WO | WO 96/29370 | 9/1996 |
| WO | WO 97/25932 | 7/1997 |
| WO | WO 00/29041 | 5/2000 |

* cited by examiner

*Primary Examiner*—Michael Mar
*Assistant Examiner*—Patrick Buechner
(74) *Attorney, Agent, or Firm*—Finnegan, Henderson, Farabow, Garrett and Dunner, L.L.P.

(57) ABSTRACT

A method for dispensing a bilogical sealant and a dispensing system for dispensing the biological sealant are described. The dispensing system comprises a dispenser and a plurality of cartridge for delivering a biological sealant to an application site. The sealant is presented as a multi-component liquid sealant, with each component contained in a cartridge comprising a tubular body closed at one end with a pierceable seal and closed at the other end by a piston element movable axially within the tubular body. The dispenser coprises a plurality of recesses to receive respective cartridges containing the components of the sealant. Each recess includes means to establish a fluid connection with the cartridge placed within the recess. The dispenser further comprises means for engaging the piston elements of the cartridges to move the piston element axially so as to expel the sealant components. Ducting within the dispenser leads the sealant components to a dispensing point.

39 Claims, 5 Drawing Sheets

BIOLOGICAL SEALANT STORAGE AND DISPENSING SYSTEM

The present invention relates to a method and apparatus for storing and dispensing multi-component mixtures, such as biological sealants.

Biological sealants have become widely used in surgical procedures as a means of preventing or reducing hemorrhage, supporting sutures or sealing cavities. Conventional sealants are prepared by mixing two ingredients. In the case of fibrin sealants, the ingredients comprise fibrinogen and thrombin, and are stored either in the form of two freeze-dried powders, or as two frozen liquids. The powders have to be prepared before use by rehydrating them with an aqueous solution, and loading the solutions into a dual syringe. The frozen liquids are prepared for use by thawing them to liquid form and loading the liquids into a dual syringe. When the solutions are mixed together, the resulting mixture immediately coagulates. By simultaneously dispensing the two components onto a wound or incision, the components mix together at the point of application, and cause clotting which reduces or prevents hemorrhage from severed blood vessels.

While the powder form of the two-part sealant of the prior art has an extended self life at chilled temperatures from 2 to 8° C., because the components are stored in powder form, they must be converted to liquid form for dispensing and mixing. Approximately 30 minutes before the sealants are required for use, the ingredients must be prepared for use by rehydrating them and loading them separately into syringes. Disadvantages of the frozen form of the two-part sealant are that it must be kept at freezing temperatures, and must be thawed prior to use. The components also have limited stability after thawing.

This requirement for preparation of the sealant prior to use leads to two disadvantages, firstly that the sealant is not instantly available, and secondly that the lead time for preparation is so long that operating theatre staff are likely to prepare surplus quantities of the sealant, rather than risk running out of the sealant during a procedure. This preparation of surplus quantities leads to wastage of sealant.

An alternative formulation of biological sealant has recently been discovered, in which three components of the sealant may be stored separately in liquid form under chilled conditions for an extended period. Such sealants are described in PCT publication WO 00/29041. The three components comprise respectively fibrinogen, thrombin, and factor XIII. When these components are mixed together, clotting results. It has also been discovered that the thrombin and factor XIII components may be initially mixed together, and this two-component mixture may be subsequently mixed with the fibrinogen. Storage of the components of the sealant in liquid form has the advantage that the components are instantly available for use, without the need to prepare the components by rehydrating or thawing them. The sealant can therefore be prepared extemporaneously and wastage is reduced.

The present invention seeks to provide a storage container and dispensing methods and apparatus for use with a multi-component mixture such as a three-component biological sealant wherein the components are in liquid form, or are frozen and can be transformed directly into the liquid state showing afterwards an increased storage stability compared to current commercial products. Furthermore, a sequence of mixing the components of a multi-component sealant is provided.

In a preferred form of the storage container of the present invention, the container comprises a tubular body having a first end closed by a pierceable seal, and having its other end sealed by a piston element movable axially relative to the tubular body.

In a preferred form of the dispenser, the dispenser comprises a plurality of recesses for receiving respective cartridges containing respective components of the mixture to be dispensed, means for establishing a fluid connection with the first ends of the cartridges, duct means for transporting components of the mixture from the cartridges to a dispensing point, and means for engaging the piston elements to move the piston elements axially towards the first ends of their respective cartridges.

The means for moving pistons in the cartridges may be a trigger and linkage mechanism, or a manually operated pushrod.

The present invention also seeks to provide a storage and dispensing apparatus for multi-component mixtures wherein the components are stored separately, and wherein two or more components of the mixture are first combined and are then mixed with at least one other component to form the final mixture.

The present invention also seeks to provide a coupling which enables two tubular components to be sealingly joined without relative rotation of the tubular components about their axes.

Embodiments of the invention will now be described in detail, with reference to the accompanying drawings, in which.

Figure 1:
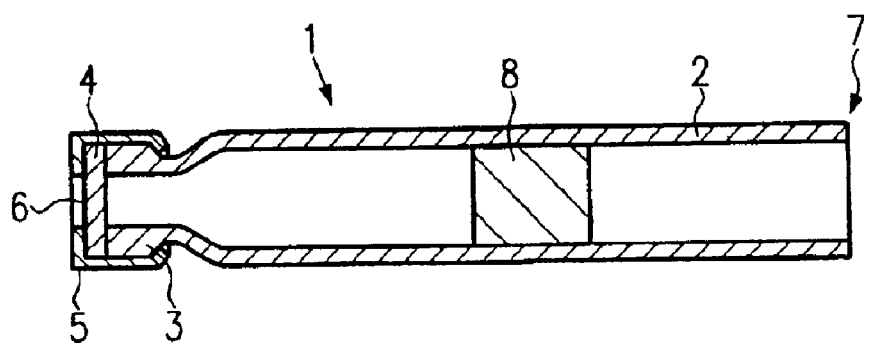
FIG. 1 is a longitudinal cross sectional view of a storage container for a liquid component of the sealant.

Referring now to the drawings, FIG. 1 is a longitudinal cross sectional view of a container or cartridge 1 for storing a component of a multi-component sealant. The cartridge comprises a tubular body 2, having a neck 3 at the left-hand end (as seen in FIG. 1). A sealing element or septum 4 seals the open end of the neck 3, and is held in place by a crimped metal cap 5. The metal cap 5 has a central opening 6 aligned with the neck 3 of the cartridge, through which a needle or cannular may be inserted to pierce the septum in order to provide fluid communication with the interior of the cartridge. The rear end 7 of the cartridge body 2 remote from the neck 3 is open, and a piston 8 is a sliding sealing fit within the tubular body.

The cartridge 1 is filled by first placing the piston 8 within the tubular body 2 at an appropriate axial position, usually adjacent the rear end 7. The cartridge is then oriented with its rear end downwards, and the liquid component is introduced through the neck 3 to fill the cartridge 1. The piston 8 sealingly engages the interior of the tubular body 2, to prevent the escape of liquid. When cartridge is full, the septum 4 is placed over the neck 3, and the metal cap 5 is placed over the septum 4 and crimped in place.

Figure 2:
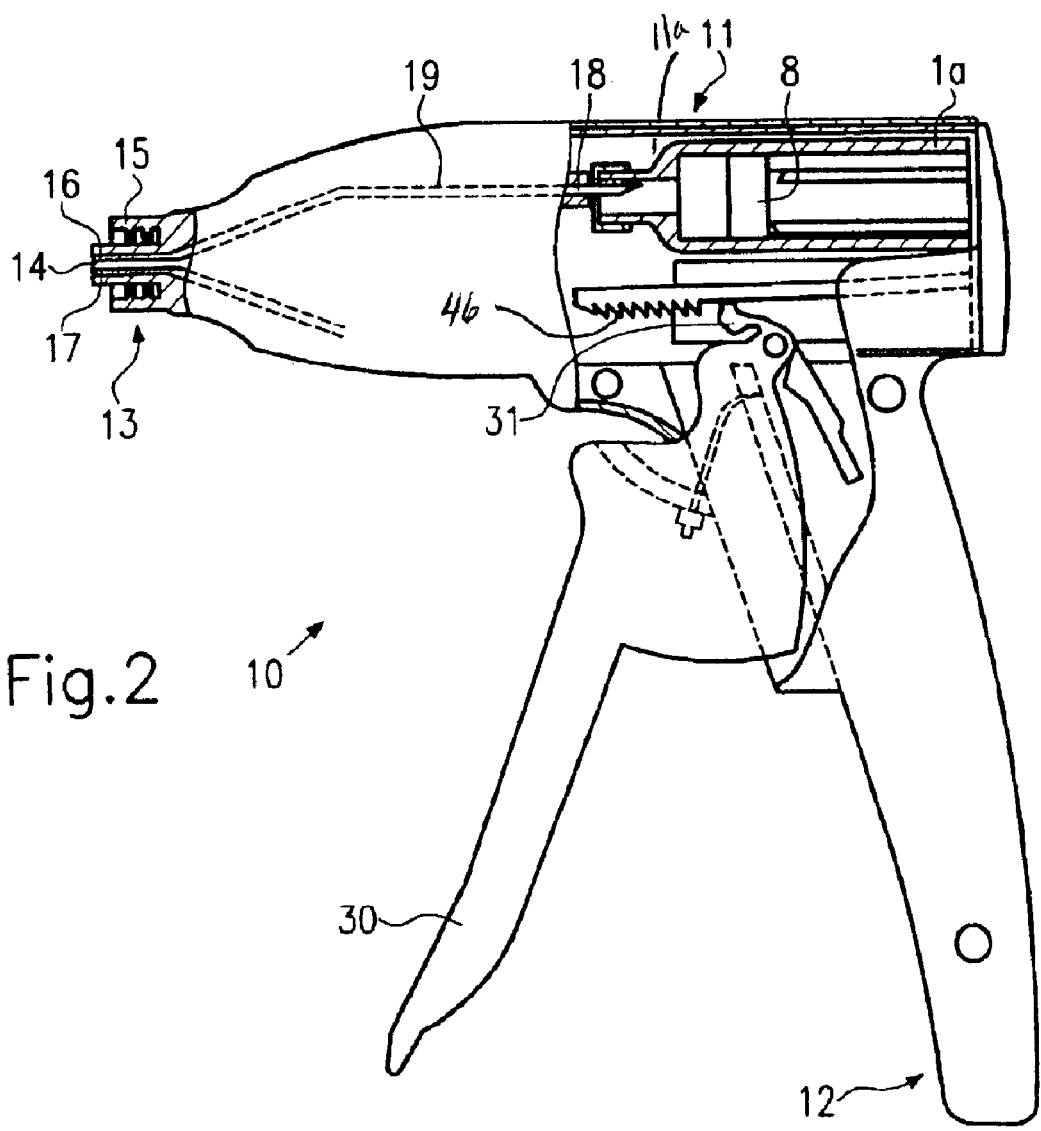
FIG. 2 is a schematic sectional view of a dispenser for simultaneously delivering components of the sealant.

FIGS. 2 to 5 are schematic views of a dispenser for use with cartridges as illustrated in FIG. 1. The dispenser 10 comprises a receiver section 11, from which a fixed butt section 12 extends downwards (as seen in FIG. 2) to form part of a gripping portion.

The receiver section 11 comprises at its front end a "Luer"-type connection 13 having a central conical boss 14 surrounded by an internally threaded sleeve 15. The central boss 14 is penetrated by upper and lower bores 16 and 17, which open at the end surface of the boss 14.

At the rear end of the receiver section 11, there are provided three cylindrical recesses 11a, 11b, 11c, each of which is adapted to receive a cartridge 1a, 1b, 1c, respectively, containing a component of a sealant. In the embodiment shown, a larger cartridge containing fibrinogen is arranged above a pair of smaller cartridges containing thrombin and factor XIII, respectively. Other proportions and combinations are however possible. Withing the receiver 11, non-coring needles 18 (only one of which is shown) are mounted so as to extend into each of the cylindrical recesses 11a, 11b, 11c, so that when a cartridge 1 is placed into the recess, the needle 18 passes through the opening 6 in the metal cap 5, penetrates the septum 4, and establishes fluid connection with the interior of the cartridge 1.

In the dispenser shown in FIG. 2, the needle 18 is connected to the upper bore 16 in the boss 14 of the Luer connection 13 by a duct 19. The lower bore 17 in the boss 14 of the Luer connection 13 is connected to the respective needles 18 mounted in the lower recesses at the rear end of the receiver 11 by the arrangement of bores schematically shown in FIG. 4. In this arrangement, the lower bore 17 is connected to the midpoint of a transverse bore 20, and the ends of the transverse bore 20 are respectively connected by means of ducts 21b and 21c to the needles 18 which penetrate the cartridges 1b and 1c positioned in the lower recesses of the receiver 11.

When the cartridges have been positioned in their respective recesses, and have thus established fluid communication between their respective interiors and the distal end of the boss 14, the components of the sealant are dispensed by advancing the pistons 8 of the cartridges towards the front of the receiver 11. In the embodiment shown in FIG. 2, this is achieved by means of a driver component 40 operated by a trigger 30 pivotally mounted to the receiver 11, in front of the butt section 12. A resilient spring biases the trigger 30 away from the butt section 12.

As seen in FIG. 2, the upper end of the trigger 30 comprises an upwardly-extending pawl 31 which moves towards the front end of the receiver 11 as the trigger 30 is squeezed towards the butt section 12.

The drive component 40 comprises an end plate 41 substantially corresponding in shape to the cross-sectional shape of the receiver 11. Three driving rods 42, 43 and 44 extend perpendicularly to the driving plate 41, and are disposed to correspond with the spacing of the recesses in the receiver 11 which receive the cartridges 1a, 1b, and 1c. Extending parallel to the driving rods 42, 43 and 44 is a draw bar 45, which is fixed to the driving plate 41 and is provided with a series of transversely extending ratchet teeth 46 on its underside.

The dispenser is prepared for use by inserting the cartridges into the recesses in the rear of the receiver 11, and then advancing the drive component 40 such that the draw bar 45 enters the rear of the receiver 11 between the cartridges 1b and 1c and the cartridge 1a. Continued insertion of the drive component 40 causes the drive rods 42, 43 and 44 to enter the open ends 7 of the cartridges 1a, 1b and 1c, respectively, and to advance therein so that the ends of the driving rods each contact the piston 8 within their respective cartridge. The length of the draw bar 45 is so arranged that, when the drive rods contact the pistons of the full cartridges, the pawl 31 of the trigger 30 engages the ratchet teeth 46 of the draw bar adjacent the free end of the draw bar.

The user then squeezes the trigger 30 towards the butt section 12, thus advancing the pawl 31 towards the front end of the receiver 11. This urges the draw bar 45 to the left (as seen in FIG. 2), drawing the end plate 41 towards the receiver 11. Drive rods 42, 43 and 44 engage the pistons 8 of the cartridges and urge them along the interiors of the cartridges to expel the components of the sealant through their respective needles 18 and ducts 19 and 16 and 21b, 21c, 20, and 17 to discharge the components of the sealant from the end face of the Luer coupling. A single-lumen cannula or other applicator device may be attached to the Luer coupling 13, to direct the mixture to the application site. However, since the mixture coagulates when the three components are mixed, such a single-lumen cannula can only have a short length if it is not to be blocked by coagulated sealant.

When all of the sealant components have been discharged from the cartridges, the dispenser and used cartridges may be discarded. Alternatively, a disengagement means may be provided whereby the pawl 31 can be disengaged from the ratchet teeth 46 of the draw bar 45, to enable a user to withdraw the drive plate 41 from the receiver 11. When the drive plate 41 has been removed, the spent cartridges may be withdrawn from the receiver 11 and discarded, and the dispenser may then be cleaned and sterilized for re-use.

A further advantage of the provision of disengagement means is that the sealant may be dispensed in two operations if required. With the ducting arrangement shown in FIG. 4, the dispenser may be assembled with only the upper cartridge 1a in position, and the drive component 40 may then be fitted to the receiver. Movement of the trigger 30 will then dispense only one component of the sealant from the upper bore 16 of the Luer coupling 13. When the first component has been applied to the treatment site, the pawl 31 can be disengaged from the ratchet teeth 46 and the drive component 40 removed from the receiver 11. The cartridges 1b and 1c containing the other two components of the sealant may then be mounted in their respective recesses, and the drive component 40 replaced so that further operation of the trigger will dispense the remaining two components of the sealant as a mixture from the lower bore 17 of the Luer coupling. The cartridge 1a may be left in position during this second dispensing operation, since its piston 8 will not contact the drive rod 42 until the contents of the lower cartridges 1b and 1c have been fully dispensed.

Figure 3:
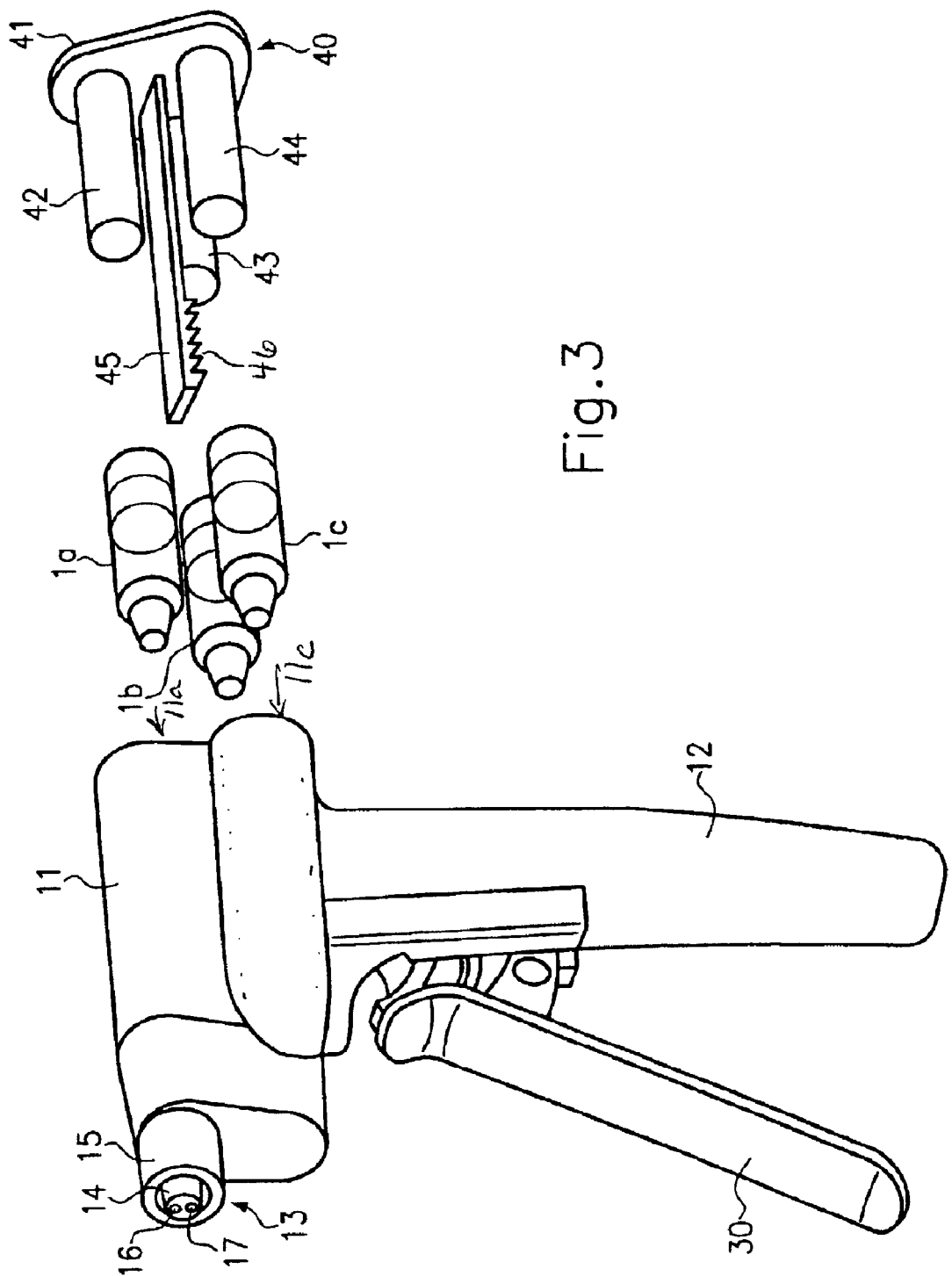
FIG. 3 is an exploded perspective view of a dispenser, cartridges, and driver portion aligned for loading, according to one aspect of the present invention.
Figure 5:
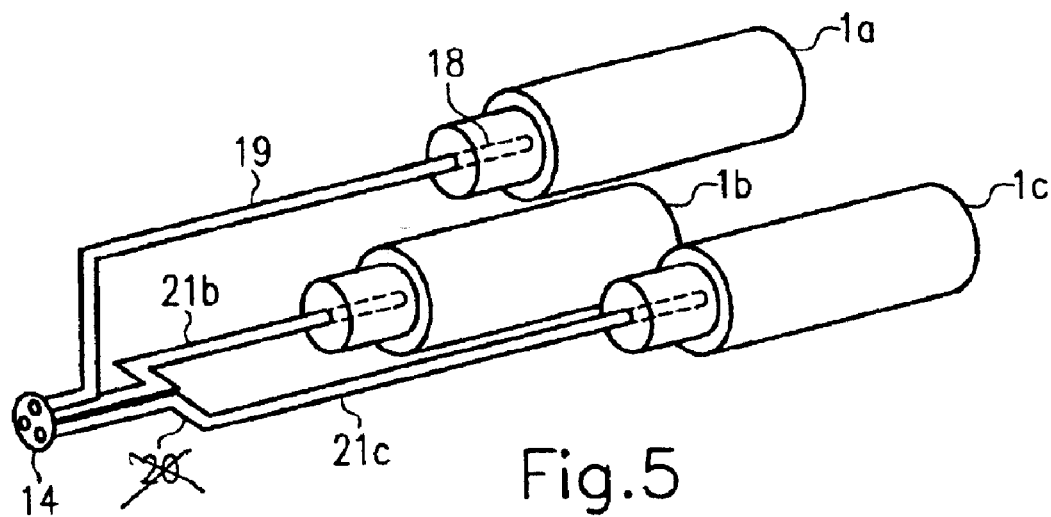
FIG. 5 is a schematic perspective view of a second arrangement for the internal ducting of the dispenser of FIG. 2.

In the embodiments shown in FIGS. 2 and 3, the boss 14 of the Luer coupling 13 has two exit bores. An alternative arrangement for the internal ducting of the receiver is shown in FIG. 5, wherein each cartridge is connected to the boss 14 of the lower coupling by a separate bore, so that three exit openings are present on the end face of the boss 14. In this arrangement, the three components are kept totally separate within the dispenser. Furthermore, a dispenser with the ducting arrangement of FIG. 5 can be used to dispense any of the components of the sealant singly, or in combination with any other one of the components of the sealant, by loading one or two cartridges only. If the disengagement means are provided to permit removal of the drive component 40, the third component may be dispensed sequentially from the same dispenser.

The dispensers described above are suitable for dispensing the sealant either directly onto the treatment site, or through a short single-lumen catheter. If the dispenser is to be held distant from the application site, for example in a "keyhole surgery" procedure where the sealant must be delivered to a site within the patient's body, then mixing of the components of the sealant within the delivery catheter must be prevented and a dual-lumen catheter is required. Such a dispenser is shown in FIG. 6, with its ducting arrangement shown in FIG. 7 and the means of connecting the dual lumen catheter seen in FIG. 8.

Figure 7:
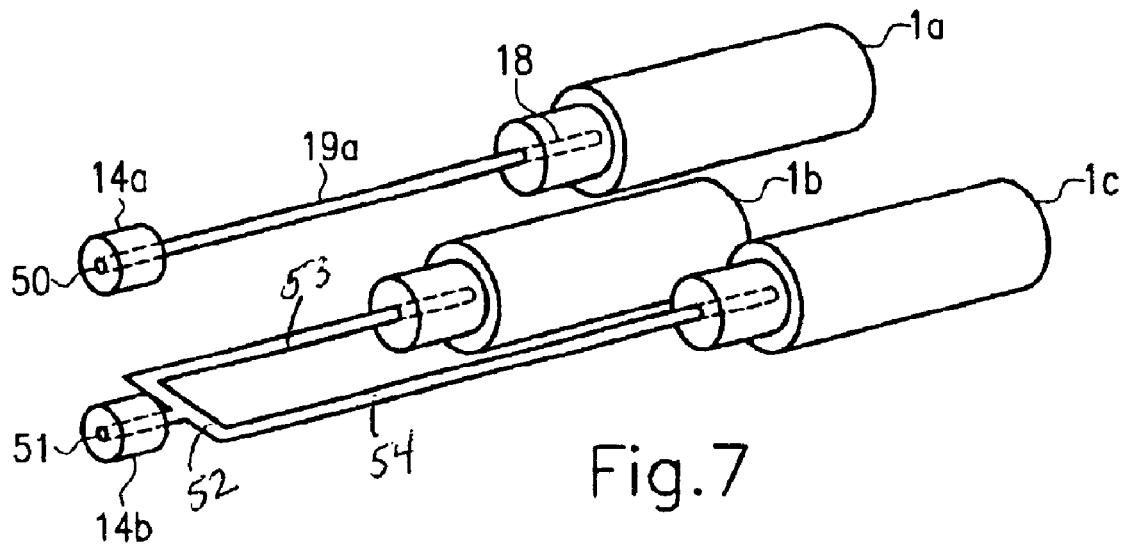
FIG. 7 is a schematic perspective view of an arrangement for the internal ducting of the dispenser of FIG. 6.
Figure 6:
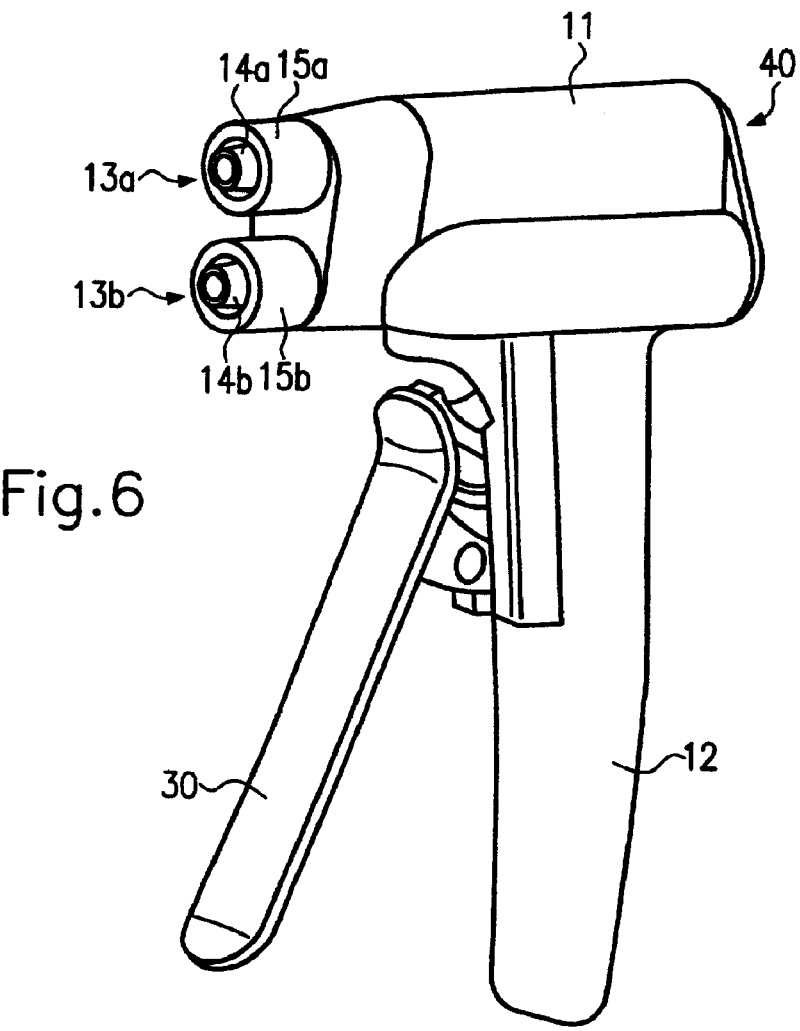
FIG. 6 is a perspective view of a second embodiment of the dispenser.

Referring now to FIGS. 6 and 7, the structure of the dispenser is substantially the same as has been described in relation to FIGS. 2 and 3. The receiver 11 of the dispenser of FIG. 6 is provided with upper and lower Luer connections 13a and 13b at its front end. The upper Luer connection 13a has a central boss 14a penetrated by a single bore 50 which is in direct fluid connection via a duct 19a with a needle 18 cooperable with the upper one 1a of the three cartridges. The lower Luer connection 13b has a central boss 14b penetrated by a single bore 51 which, via transverse bore 52 and longitudinal bores 53 and 54, is in communication with both of the lower cartridges 1b and 1c. The cylindrical sleeves 15a and 15b surrounding the respective bosses 14a and 14b of the upper and lower Luer couplings are not fixed to the receiver, but are mounted to the receiver so as to be rotatable about their respective axes yet held against movement in their respective axial directions away from the receiver 11.

Figure 8:
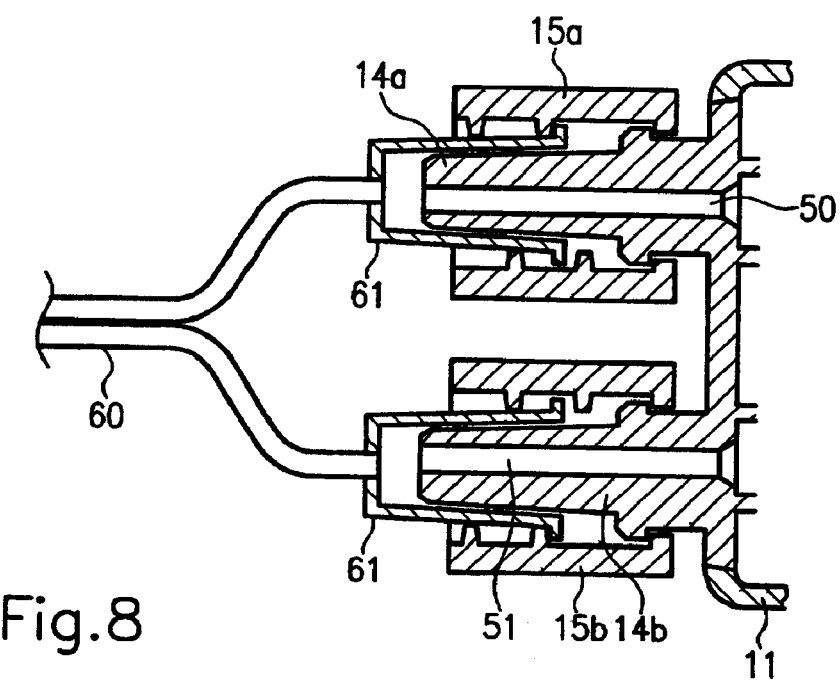
FIG. 8 is a fragmentary cross sectional view of a dual lumen catheter connected to the dispenser of FIG. 6.
Figures 9A, 9B:
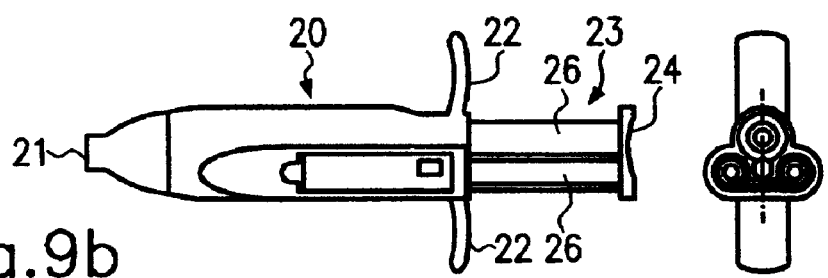
FIGS. 9a, 9b and 9c are an end view, a sectional side view and a top view of a third embodiment of the dispenser, respectively.
Figure 9C:
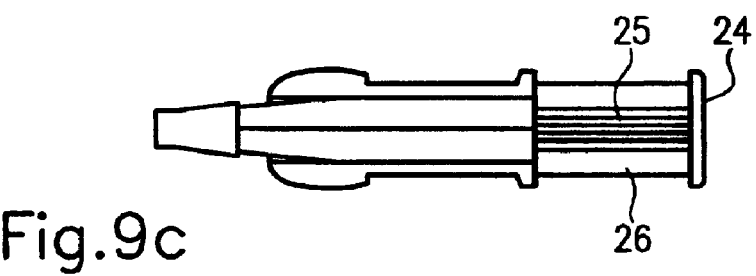

A connector for joining a dual-lumen catheter 60 to the dispenser is illustrated in section in FIG. 8. Each lumen of the catheter 60 is provided with a female Luer connection 61, which comprises a conical cup-like component having a radially outwardly extending flange at its open end, and the lumen of the catheter extending axially from its closed end. The sleeves 15a and 15b of the upper and lower Luer connections have internal threaded surfaces engageable with the flanges of the female Luer connections. The sleeves each have an internal flange at the end nearest the receiver 11, which engages with a radially outwardly extending abutment surface at the base of the boss 14 to limit axial movement of the sleeves 15 away from the receiver 11. To connect the dual-lumen catheter, the open ends of the respective female Luer connections 61 are placed over the bosses of the upper and lower Luer connections of the dispenser. By rotating the sleeves, the threads of the sleeves engage the flanges of the female Luer connections and draw the Luer connections down onto the bosses to form a fluid-tight seal. By making the sleeves 15 rotatable relative to the bosses 14, it is not necessary to rotate the female Luer couplings while the connection is being made. This will avoid any strain or breakage of the dual-lumen catheter caused by such a twisting movement.

It will be understood that only one of the two Luer connections may be provided with a rotatable sleeve 15, the other Luer being provided with a conventional fixed sleeve. In this case, the Luer with the fixed sleeve is first connected to the catheter by rotation of the catheter, and the Luer with the rotatable sleeve is then connected by rotating the sleeve 15.

The operation of the dispenser is as described above, with the difference that the fibrinogen component will be dispensed from the upper Luer connector 13a, and the mixed thrombin and factor XIII components will be dispensed from the lower Luer connector 13b. Since the thrombin and factor XIII components may be mixed without clotting, the mixture may be delivered through one lumen of a dual lumen catheter while the fibrinogen component is delivered through the other lumen to an application site, by connecting the respective lumens of the catheter to the respective Luer couplings of the dispenser. This principle allows the application of fibrinogen and thrombin/factor XIII in comparable volumes, which is important for catheters having two lumens of equal cross sections, so that the components all reach the distal end of the catheter at the same time at the start of application. The principle of pre-mixing the factor XIII and the thrombin also improves homogeneity of the final mixture and allows the use of existing two-channel dispensing tips.

The dual-lumen catheter described above may be substituted by a three-lumen catheter, with two of the lumens connected to the dispenser as described above and the third lumen attached to a regulatable supply of compressed air or other gas. The gas discharging at the distal end of the catheter forms a spray with the dispensed sealant components, promoting a wide and even coverage of the area to be treated.

In a further embodiment of the invention, not illustrated, the receiver of the dispenser may be provided at its front end with three Luer couplings as described in relation to FIGS. 6 and 8, and the internal ducting of the receiver may be arranged such that each Luer coupling is connected to a respective one of the three component cartridges. A triple-lumen catheter may then be connected to the dispenser in a manner analogous to that illustrated in FIG. 8, so that all three components of the sealant may be delivered separately, and mixed only at the application site.

In a further alternative embodiment of the coupling, the female Luer connectors of a multi-lumen catheter may be provided with rotatable sleeves which have an internal flange at one end for engaging the external flange of the female Luer connector, and an internal or external thread at the other end for engaging a complementary threaded structure surrounding the boss of the male Luer connector formed on the receiver. The connection would then be made by placing the cup of the female Luer connector over the boss of the male Luer connector, and subsequently threadedly engaging the rotatable sleeve of the female Luer connector with the complementary threaded structure so that the internal flange of the sleeve engages the external flange of the female Luer connector to draw it into close engagement with the boss of the male Luer connector.

Figure 4:
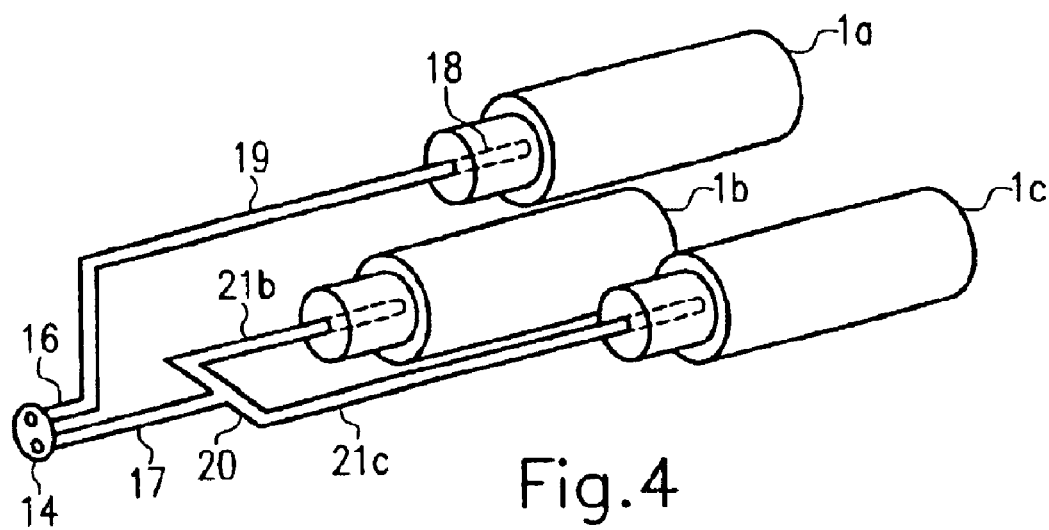
FIG. 4 is a schematic perspective view of a first arrangement for the internal ducting of the dispenser of FIG. 2.

In the ducting arrangements shown in FIGS. 4 and 7, mixing of the thrombin and factor XIII components may be promoted by providing a mixing chamber (not shown) at the confluence of the ducts from the respective needles 18 of these components of the sealant. By leading the components into a swirl chamber in tangential directions, mixing of the two components may be improved and an intimate mixture delivered to the Luer connection.

To assist a user in determining how much of the sealant remains in the dispenser, cartridges may be formed from transparent material such as glass or plastics, and the sidewalls of the receiver may be formed with cutouts or windows through which the pistons 8 fo the cartridges are visible. The pistons 8 may be brightly colored for ease of visibility. Alternatively, markings may be provided on the drive rods of the drive component 40 to indicate how far the drive component has been advanced into the receiver 11.

The ratchet and pawl mechanism operative between the trigger and the draw bar may be such that several activations of the trigger are necessary in order completely to advance the drive component into the receiver. Although a ratchet and pawl mechanism is described in relation to the above embodiments, any suitable mechanism may be used such as a rack and pinion or the trigger may be a simple lever engaging an abutment on the draw bar.

The receiver, trigger and drive component are preferably moulded from plastics material, with the highly stressed parts of the assembly such as the ratchet teeth and the pawl being constructed from suitable hard materials. Alternatively, the pawl and draw bar may be metallic components. The relative positioning of the draw bar and the drive rods on the drive plate is preferably such that the reaction forces acting on the drive rods and the tension in the draw bar give rise to little or no net moment on the drive plate.

Referring now to FIGS. 9a–c and 10a and 10b, there is shown an alternative embodiment of the dispenser for a three-component biological sealant. The dispenser comprises a receiver section 20 having a Luer type connection 21 at a leading end of the receiver 20. A trailing end of the receiver 20 is provided with finger grips 22 extending laterally from the receiver. The trailing end of the receiver 20 is provided with three recesses, for accommodating three cartridges containing the respective components of the sealant in a manner similar to that described in relation to the previous embodiment. Each recess is provided with a non-coring needle (not shown) and internal ducting is provided to connect the three non-coring needles to the Luer type connection 21, in a manner similar to the arrangements illustrated in FIGS. 4 and 5 in relation to the previous embodiment.

Figures 10A, 10B:
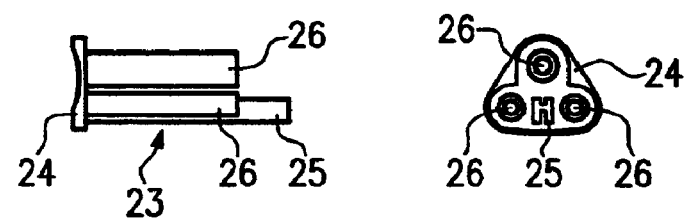
FIGS. 10a and 10b are end and side views, respectively, of a pushrod for the dispenser of FIGS. 9a–9c.

A piston assembly 23, comprising a pusher plate 24, a guide post 25 of an "H" shaped cross-section and three driving rods 26 is seen in end view in FIG. 10a and in side view in FIG. 10b. The driving rods 26 are arranged so as to be engageable with the three recesses in the receiver section 20, and the guide post 25 is received in a correspondingly-shaped fourth recess extending from the trailing end of the receiver 20.

In use, three cartridges containing the respective components of the sealant are placed in respective ones of the three recesses, and the free end of the guide post 25 is engaged with its recess in the receiver 20. It will be appreciated that, since the guide post 25 is longer than the driving rods 26, the guide post can be engaged with the receiver 20 before the guide posts 26 enter their respective recesses to engage the pistons of their respective cartridges.

By grasping the finger grips 22 of the receiver and applying pressure to the plate 24 of the piston assembly, the piston assembly may be moved into the receiver 20, whereupon the three driving rods 26 advance the pistons in the respective cartridges to expel the components of the sealant through the ducting and out of the Luer connection 21. The guide post 25 and its corresponding recess may be formed with cooperating latch means which prevent removal of the piston assembly after it has been fully advanced into the receiver 20. This will ensure that the equipment is discarded after a single use. Alternatively, if a two-stage application of the sealant components is desired, the piston assembly 23 may be removable from the receiver 20 so that in a first operation one or two components of the sealant may be delivered, the piston assembly then being removed, and full cartridges of the remaining components being inserted into their respective recesses. The piston assembly 23 is then replaced and a further dispensing operation carried out to dispense the remaining component or components of the sealant.

In a variation of this second embodiment (not illustrated) a ducting arrangement similar to that shown in FIG. 7 may be adopted, and the leading end of the receiver 20 may be provided with two Luer-type connections 21.

The cartridges are preferably manufactured from glass, but may be made from stainless-steel or any suitably stable plastics material such as cyclo-olefin copolymer. As an alternative to providing a pierceable septum at the neck end of the cartridge and a needle in the receiver, the cartridge and the receiver may be provided with male and female Luer connections or any other suitable sealing connection. The diameters of the cartridges may be so arranged that equal axial movements of their respective pistons displace proportionate amounts of the components contained in the cartridges. The cartridges and their respective recesses in the receiver are preferably so configured that incorrect insertion of the cartridges is prevented. While the cross-sectional shape of the cartridges is circular in the described embodiments, it is to be understood that elliptical, triangular, square, rectangular or other non-circular cross-sectional shapes may be used, with correspondingly shaped pistons, and recesses in the receivers of the dispensers may be so configured as to receive only one shape of cartridge to prevent mis-installation of cartridges.

The cartridges may additionally be provided with means to prevent egress of the piston from the open second end of the cartridge. In some sterilization procedures, such as ethylene oxide sterilization, the cartridges are exposed to an ambient pressure less than atmospheric, i.e. possibly less than the pressure within the cartridge. This pressure difference may cause the piston to move towards, or even out of, the second end of the cartridge.

What is claimed is:

1. An apparatus for dispensing a multi-component biological sealant, comprising:

a plurality of sealant cartridges for containing respective components of the sealant, each sealant cartridge including a substantially tubular body having a first end closed by a seal and a second end sealed by an axially-movable piston element; and a dispenser for dispensing the sealant components from the cartridges, the dispenser comprising:

a main body having a plurality of elongated recesses for receiving respective cartridges;

means for establishing fluid connection with said first end of the cartridge associated with each recess;

ducting means for transporting respective components of the sealant from said cartridges to a dispensing point;

means for engaging the piston elements to move the piston elements axially towards said first ends of their respective cartriges; and a drive mechanism connected to the means for engaging the piston elements and configured to assist in moving the means for engaging the piston elements.

2. An apparatus according to claim 1, wherein the seal closing each cartridge at its first end is a pierceable septum, and the means for establishing fluid connection comprises a non-coring needle.

3. An apparatus according to claim 1, wherein each cartridge has a Luer connection at its first end, and the means for establishing fluid connection comprises a complementary Luer connection.

4. An apparatus according to claim 1, wherein the means for engaging the piston elements comprises a drive plate including a plurality of push rods, each of the push rods configured to engage a respective piston element.

5. An apparatus according to claim 4, wherein the drive plate has an elongate guide element receivable in a guide recess in the main body of the dispenser for guiding movement of the drive plate.

6. An apparatus according to claim 1, wherein the means for establishing fluid connection with said first end of a cartridge and associated with each recess is located in each recess of the dispenser and are each independently connected to the dispensing point by a respective duct.

7. An apparatus according to claim 6, wherein the dispensing point comprises a single Luer connection connected to all of the recesses.

8. An apparatus according to claim 6, wherein the dispensing point comprises a first Luer connection connected to one of the recesses, and a second Luer connection connected to one or more of the remaining recesses.

9. An apparatus according to claim 1, wherein the cartridges are formed from transparent material, and wherein windows are formed in the body of the dispenser so that the amount of material present in a cartridge within a recess of the dispenser body may be visually determined.

10. An apparatus according to claim 1, wherein the cartridges for respective components of the sealant are of substantially equal axial length, and wherein the cartridges each have a different cross-sectional area.

11. An apparatus according to claim 1, wherein the cartridges have a substantially circular cross-section.

12. An apparatus according to claim 1, wherein the cartridges each have a differently shaped cross-section, and wherein the recesses in the dispenser body are each shaped to correspond with a respective one of the cross-sectional shapes of the cartridges.

13. A cartridge for use in the apparatus of claim 1, comprising a substantially tubular body having a first end closed by a pierceable seal and a second end sealed by an axially-movable piston element, and further comprising a component of a biological sealant contained between the pierceable seal and the piston element.

14. An apparatus for dispensing a multi-component biological sealant, comprising:
 a plurality of sealant cartridges for containing respective components of the sealant, each sealant cartridge including a substantially tubular body having a first end closed by a seal and a second end sealed by an axially-movable piston element; and
 a dispenser for dispensing the sealant components from the cartridges, the dispenser comprising:
  a main body having a plurality of elongated recesses for receiving respective cartridges;
  means for establishing fluid connection with said first end of the cartridge associated with each recess;
  ducting means for transporting respective components of the sealant from said cartridges to a dispensing point; and
  means for engaging the piston elements to move the piston elements axially towards said first ends of their respective cartridges, wherein the means for engaging the piston elements comprises a drive plate including a plurality of push rods, each of the push rods configured to engage a respective piston element,
  wherein the main body of the dispenser includes a drive mechanism cooperable with the drive plate to move the drive plate in the axial direction toward the recesses.

15. An apparatus according to claim 14, wherein the drive mechanism is disengageable from the drive plate to permit movement of the drive plate in the axial direction away from the recesses.

16. An apparatus according to claim 14, wherein the main body of the dispenser includes a pawl and the drive plate comprises a ratchet, the pawl being engageable with the ratchet to move the drive plate toward the recesses.

17. An apparatus for dispensing a multi-component biological sealant, comprising:
 a plurality of sealant cartridges for containing respective components of the sealant, each sealant cartridge including a substantially tubular body having a first end closed by a seal and a second end sealed by an axially-movable piston element; and
 a dispenser for dispensing the sealant components from the cartridges, the dispenser comprising:
  a main body having a plurality of elongated recesses for receiving respective cartridges;
  means for establishing fluid connection with said first end of the cartridge associated with each recess;
  ducting means for transporting respective components of the sealant from said cartridges to a dispensing point; and
  means for engaging the piston elements to move the piston elements axially towards said first ends of their respective cartridges,
  wherein three recesses are provided in the dispenser to accommodate cartridges containing three components of a biological sealant, and wherein the means for establishing fluid connection and associated with two of the recesses have first and second cartridges located therein are connected to the dispensing point by a common duct, and wherein the means for establishing fluid connection and associated with the third recess have a third cartridge connected to the dispensing point by a separate duct.

18. An apparatus according to claim 17, wherein said dispenser includes a mixing chamber to receive components of the biological sealant from cartridges in said two recesses, and to supply a mixture of the two components to the common duct.

19. An apparatus according to claim 17, wherein the dispensing point comprises a first Luer connection at which the common duct opens, and a second Luer connection at which the separate duct opens.

20. An apparatus according to claim 19, wherein the first and second Luer connections comprise a conical central portion and an internally-threaded collar axially retained in relation to the conical central portion and rotatable relative thereto.

21. A dispenser for use in an apparatus for dispensing a biological sealant having multiple sealant components, each of the sealant components being contained in a cartridge having a substantially tubular body with a first end closed by a pierceable seal and a second end sealed by an axially-movable piston element, wherein the dispenser comprises:
 a main body having a plurality of elongated recesses for receiving respective cartridges containing the respective sealant components and a dispensing point for delivering the sealant components;
 means for establishing fluid connection with said first end of the cartridge associated with each recess;
 ducting means for transporting respective components of the sealant from said cartridges to the dispensing point;
 means for engaging the piston elements to move the piston elements axially towards said first ends of their respective and cartridges; and a drive mechanism connected to the means for engaging the piston elements and configured to assist in moving the means for engaging the piston elements.

22. A dispenser according to claim 21, wherein the means for establishing fluid connection comprises a non-coring needle.

23. A dispenser according to claim 21, wherein the means for establishing fluid connection comprises a Luer connection.

24. A dispenser according to claim 21, wherein the means for engaging the piston elements comprises a drive plate including a plurality of push rods, each of the push rods configured to engage a respective piston element.

25. A dispenser according to claim 24, wherein the drive plate has an elongate guide element receivable in a guide recess in the main body of the dispenser for guiding movement of the drive plate.

26. A dispenser according to claim 21, wherein each recess is independently connected to the dispensing point by a separate duct.

27. A dispenser according to claim 21, wherein the dispensing point comprises a single Luer connection connected to all of the recesses.

28. A dispenser according to claim 21, wherein the dispensing point comprises a first Luer connection connected to one of the recesses, and a second Luer connection connected to at least one of the remaining recesses.

29. A dispenser according to claim 28, wherein the main body includes three recesses to accommodate three cartridges, each cartridge containing one of three components of a biological sealant, and wherein two of the recesses of the dispenser are connected to the dispensing point by a common duct, and the third recess is connected to the dispensing point by a separate duct.

30. A dispenser according to claim 29, further comprising a mixing chamber having respective inlets connected to said two recesses, and an outlet connected to the common duct.

31. A dispenser according to claim 29, wherein the dispensing point comprises a first Luer connection at which the common duct opens, and a second Luer connection at which the separate duct opens.

32. A dispenser according to claim 31, wherein at least one of the first and second Luer connections comprises a conical central portion and an internally-threaded collar axially retained in relation to the conical central portion and rotatable relative thereto.

33. A dispenser according to claim 32, wherein the first and second Luer connections comprise a conical central portion and an internally-threaded collar axially retained in relation to the conical central portion and rotatable relative thereto.

34. A dispenser for use in an apparatus for dispensing a biological sealant having multiple sealant components, each of the sealant components being contained in a cartridge having a substantially tubular body with a first end closed by a pierceable seal and a second end sealed by an axially-movable piston element, wherein the dispenser comprises:

a main body having a plurality of elongated recesses for receiving respective cartridges containing the respective sealant components and a dispensing point for delivering the sealant components;

means for establishing fluid connection with said first end of the cartridge associated with each recess;

ducting means for transporting respective components of the sealant from said cartridges to the dispensing point; and means for engaging the piston elements to move the piston elements axially towards said first ends of their respective cartridges, wherein the means for engaging the piston elements comprises a drive plate including a plurality of push rods, each of the push rods configured to engage a respective piston element, wherein the main body of the dispenser comprises a drive mechanism cooperable with the drive plate to move the drive plate in the axial direction toward the recesses.

35. A dispenser according to claim 34, wherein the drive mechanism is disengageable from the drive plate to permit movement of the drive plate in the axial direction away from the recesses.

36. A dispenser according to claim 34, wherein the main body of the dispenser includes a pawl and the drive plate comprises a ratchet, the pawl being engageable with the ratchet to move the drive plate toward the recesses.

37. An apparatus for dispensing a multi-component biological sealant, comprising:

a plurality of sealant cartridges for containing respective components of the sealant, each sealant cartridge including a substantially tubular body having a first end closed by a seal and a second end sealed by an axially-movable piston element; and a dispenser for dispensing the sealant components from the cartridges, the dispenser comprising:

a main body having a plurality of elongated recesses for receiving respective cartridges;

means for establishing fluid connection with said first end of the cartridge associated with each recess;

ducting means for transporting respective components of the sealant from said cartridges to a dispensing point; and means for engaging the piston elements to move the piston elements axially towards said first ends of their respective cartridges, wherein three recesses are provided in the dispenser to accommodate cartridges containing three components of a biological sealant.

38. An apparatus according to claim 37, wherein the means for establishing fluid connection and associated with two of the recesses have first and second cartridges located therein are connected to the dispensing point by a common duct.

39. An apparatus according to claim 38, wherein the means for establishing fluid connection and associated with the third recess have a third cartridge connected to the dispensing point by a separate duct.

* * * * *

UNITED STATES PATENT AND TRADEMARK OFFICE
CERTIFICATE OF CORRECTION

PATENT NO. : 6,874,657 B2  
DATED : April 5, 2005  
INVENTOR(S) : Hubert J. Metzner et al.

It is certified that error appears in the above-identified patent and that said Letters Patent is hereby corrected as shown below:

Title page,
Item [57], ABSTRACT,
Line 1, "bilogical" should read -- biological --;
Line 10, "coprises" should read -- comprises --;
Line 15, "piston element" should read -- piston elements --.

Column 8,
Line 54, "cartriges;" should read -- cartridges; --.

Column 10,
Line 67, "respective and cartridges" should read -- respective cartridges --.

Signed and Sealed this

Thirteenth Day of September, 2005

JON W. DUDAS
*Director of the United States Patent and Trademark Office*